United States Patent
Weinert et al.

(10) Patent No.: US 8,123,717 B2
(45) Date of Patent: Feb. 28, 2012

(54) THERAPY DELIVERY SYSTEM HAVING AN OPEN ARCHITECTURE AND A METHOD THEREOF

(75) Inventors: Stefan Weinert, Pendleton, IN (US); Ajay Thukral, Indianapolis, IN (US); Paul Galley, Cumberland, IN (US); Siva Chittajallu, Indianapolis, IN (US); Steven Bousamra, Carmel, IN (US); James Long, Fishers, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 32 days.

(21) Appl. No.: 12/121,199

(22) Filed: May 15, 2008

(65) Prior Publication Data
US 2009/0005728 A1    Jan. 1, 2009

Related U.S. Application Data

(60) Provisional application No. 60/946,645, filed on Jun. 27, 2007.

(51) Int. Cl.
*A61M 31/00*    (2006.01)

(52) U.S. Cl. .......................................... 604/66; 703/11
(58) Field of Classification Search .............. 604/890.1, 604/891.1, 504, 503, 65–67; 703/11
See application file for complete search history.

(56) References Cited

U.S. PATENT DOCUMENTS

| | | | |
|---|---|---|---|
| 5,088,981 A * | 2/1992 | Howson et al. .............. 604/31 |
| 2003/0212379 A1* | 11/2003 | Bylund et al. ............... 604/504 |
| 2005/0131663 A1* | 6/2005 | Bangs et al. .................. 703/11 |
| 2006/0078897 A1 | 4/2006 | Wedinger et al. |
| 2008/0154179 A1 | 6/2008 | Cantor et al. |

FOREIGN PATENT DOCUMENTS

| | | |
|---|---|---|
| WO | 0032258 A1 | 6/2000 |
| WO | 2008085421 A2 | 7/2008 |

* cited by examiner

*Primary Examiner* — Theodore Stigell
(74) *Attorney, Agent, or Firm* — Dinsmore & Shohl LLP

(57) ABSTRACT

A therapy delivery system having an open architecture and method of providing thereof are disclosed. The present invention provides a therapy dosage module having a control algorithm that can be replaced with a predefined or independently defined control algorithm. The tools necessary to create and test such control algorithms in the therapy dosage module in a simulated environment before implementing it in a live therapy system are also disclosed.

22 Claims, 5 Drawing Sheets

THERAPY DELIVERY SYSTEM HAVING AN OPEN ARCHITECTURE AND A METHOD THEREOF

FIELD OF THE INVENTION

The present invention relates generally to chronic disease management, and more particularly, to a therapy delivery system having an open architecture via a replaceable control algorithm that regulates therapy delivery and a method thereof.

BACKGROUND OF THE INVENTION

Prior art therapy delivery systems typically implement one or more control algorithms, which, in some instances, may be selected depending on a particular need or condition of an individual receiving therapy. In such therapy delivery systems, each algorithm provides a number of parameters which each may be populated with individualized data and/or tuned/customized within a given allowable range. However, with such systems, the logic of the algorithm in applying and using the parameters with data has been formally tested to set the allowable range of parameter values. Accordingly, the logic and ranges are unchangeable as such changes are considered non-trivial as needing further testing to see if acceptable. As algorithms are often developed from population based studies, in certain instances, such algorithms do not meet the particular needs of an individual in managing a chronic disease, such as diabetes.

SUMMARY OF THE INVENTION

It is against the above background that the present invention provides a therapy delivery system having an open architecture which in one embodiment provides a replaceable control algorithm that regulates therapy delivery and a method thereof. In other embodiments, the open architecture of the delivery system also enable parameter changes, such as for example and not limited thereto, adding/removing parameters, modifying ranges, etc., and in still other embodiments, providing both such algorithm and parameter changes. In further embodiments, the present invention permits such changes to be tested, evaluated and approve for use in the therapy deliver system and/or device.

In accordance with one embodiment of the present invention, a therapy delivery system for an individual comprises a therapy dosage module comprising a first control algorithm replaceable with a second control algorithm customized to needs of the individual, the first and second control algorithms being defined to determine therapy for the individual. The therapy delivery system also comprises a simulation module for providing a test environment simulating at least one or more physiological conditions of the individual and enabling testing of the second control algorithm when implemented in the therapy dosage module in the test environment before being used in the therapy delivery system to deliver the therapy determined by the second control algorithm to the individual.

In accordance with another embodiment of the present invention, a therapy delivery system for an individual comprises a metabolic sensor for sensing a metabolic parameter of the individual and an input/output interface for exchanging therapy-related data with the individual. In addition, the therapy delivery system comprises a therapy dosage module comprising a first control algorithm replaceable with a second control algorithm, the first and second control algorithms being defined to determine therapy for the individual, and a therapy delivery device for delivering the therapy determined by the first or second control algorithm of the therapy dosage module. The second control algorithm is customized to needs of the individual prior to determination of the therapy through testing of the second control algorithm in a test environment simulating at least one or more physiological conditions of the individual.

In accordance with another embodiment of the present invention, a method of delivering therapy to an individual with an embodiment of a therapy delivery system comprises defining a control algorithm for determining therapy for the individual, the control algorithm customized to needs of the individual; providing a simulation module providing a test environment simulating at least one or more physiological conditions of the individual; implementing the control algorithm in the test environment; applying the control algorithm to a virtual patient population in the test environment to identify any detrimental outcomes to patient health caused by the therapy determined by the control algorithm prior to usage of the control algorithm in the therapy delivery system to deliver the therapy to the individual; modifying the control algorithm as necessary to substantially eliminate the detrimental outcomes, if any, identified by the simulation module; implementing the control algorithm in the therapy delivery system; and delivering therapy to the individual with the therapy delivery system, the therapy determined by the control algorithm.

BRIEF DESCRIPTION OF THE DRAWINGS

The following detailed description of the various embodiments of the present invention can be best understood when read in conjunction with the following drawings, where like structure is indicated with like reference numerals and in which.

Figure 1:
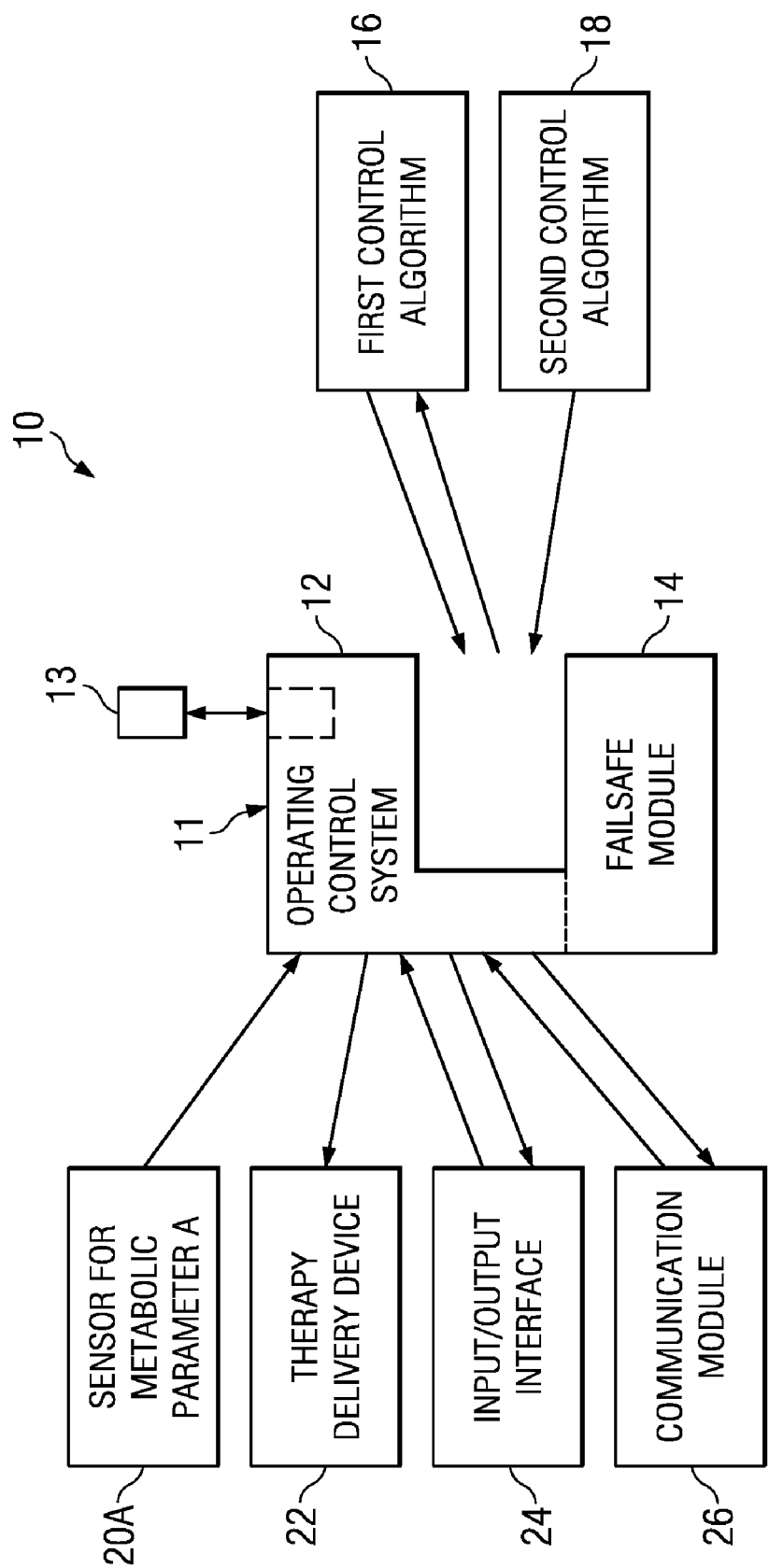
FIG. 1 is an illustration of a therapy delivery system according to one embodiment of the present invention.

The embodiments set forth in the drawings are illustrative in nature and are not intended to be limiting of the invention defined by the claims. Moreover, individual aspects of the drawings and the invention will be more fully apparent and understood in view of the detailed description.

DETAILED DESCRIPTION

Referring initially to FIG. 1, a therapy delivery system 10 for an individual generally comprises a therapy dosage module 11, a first control algorithm 16, a second control algorithm 18 that may replace the first control algorithm 16, one or more metabolic sensors 20A for sensing one or more metabolic parameters, a therapy delivery device 22, an input/output interface 24, and a communication module 26. Embodiments of the therapy delivery system 10 of the present invention generally are configured to stabilize a metabolic parameter of an individual through sensing the condition of the metabolic parameter, monitoring therapy-related data, and delivering therapy necessary for stabilization of the metabolic parameter as determined by a control algorithm factoring the sensed metabolic parameter and the monitored therapy-related data.

For exemplary purposes only, according to one embodiment, the therapy delivery system 10 is an automated pancreas device comprising a glucose sensor as the metabolic sensor 20A, an insulin pump as the therapy delivery device 22, and an insulin dosing algorithm as the first or second control algorithm 16, 18. In the illustrative embodiment, the automated pancreas device is configured to sense an individual's blood glucose concentration in a continuous or pseudo-continuous manner and to adjust the infused insulin dosage more or less continuously based on sensed blood glucose concentration values, insulin infusion history, food intake, activity levels, and/or other therapy-related data (whether monitored directly or inputted by the individual). The control algorithm 16, 18 employed by the automated pancreas device to determine appropriate insulin dosages can take on various forms, ranging from simple rule sets to elaborate adaptive model-predictive control algorithms. As such, therapy delivered to the individual by the therapy delivery system 10 is insulin in a dosage amount, concentration, delivery rate, and/or delivery schedule determined by the first or second control algorithm 16, 18.

Further details of one suitable automatic pancreas device/system is disclosed by commonly assigned and co-pending U.S. patent application Ser. No. 12/119,143, entitled "SYSTEM FOR DEVELOPING PATIENT SPECIFIC THERAPIES BASED ON DYNAMIC MODELING OF PATIENT PHYSIOLOGY AND METHOD THEREOF," which the entire disclosure thereof is herein fully incorporated by reference. While the therapy delivery system 10 is exemplified as an automated pancreas device herein, it is contemplated that the therapy delivery system 10 may be embodied in, or applied to, various other chronic disease therapy management/support systems.

The therapy dosage module 11 of the therapy delivery system 10 comprises an operating control system 12 and a failsafe module 14 having a fail-safe algorithm. One suitable example of a fail-safe module/algorithm is disclosed by commonly assigned and co-pending U.S. patent application Ser. No. 11/145,910, entitled "SYSTEM AND METHOD PROVIDING FOR USER INTERVENTION IN A DIABETES CONTROL ARRANGEMENT," and which the entire disclosure thereof is herein incorporated fully by reference. The operating system 12 may be configured to serve as a communication hub between all of other components, hardware or software, of the therapy delivery system 10, and peripherals thereto. Such communication may be transmitted to and from the operating control system 12 via a wired connection or wirelessly. In addition, the operating control system 12 may maintain time and calendar functions and synchronize all operations of the therapy control system 10. The operating control system 12 may also comprise, or communicate with, a database for storing and/or retrieving data. Further, the operating control system 12 may perform unit conversion, data synchronization, and recovery operations for the therapy delivery system 10.

The operating control system 12 is configured as having an open architecture platform that supports the operation of the therapy delivery system 10 while permitting the implementation and removal of software, including, but not limited to control algorithms, from the operating control system 12 without interfering with the operational functionality of the therapy delivery system 10. More particularly, the control algorithms 16, 18 are general software utilities that provide outputs, such as, but not limited to, recommended therapies, that are functions of time and inputs, such as, but not limited to, metabolic parameters and physiological conditions. Therefore, essentially, the control algorithms 16, 18 determine therapies in response to various triggered events. The open architecture of the operating control system 12 permits in one embodiment the replacement of one control algorithm with another to enhance therapy determination specific to changing needs of the individual using the therapy delivery system 10. In addition, the open architecture generally encapsulates a static part (i.e. the platform) of the code of the operating control system 12, enabling greater interaction between the therapy delivery system 10 and the individual using it. In other embodiments, the operating control system 12 permits parameter changes, such as for example and not limited thereto, adding/removing parameters, modifying ranges, etc., and in still other embodiments, permits both such algorithm and parameter replacement/changes.

Further, as mentioned above, in one embodiment the first control algorithm 16 is replaceable with the second control algorithm 18. This may be accomplished with the open architecture of the operating control system 12 through a logical separation of the first and second control algorithms 16, 18 from hardware and software of the therapy delivery system 10. Thereby, the second control algorithm 18 replaces the first control algorithm 16 without interfering with the operational functionality of the hardware and software of the therapy delivery system 10.

While the open architecture of the operating control system 12 of the therapy dosage module 11 of the therapy delivery system 10 is described herein as permitting the replacement/changing of control algorithms, it is contemplated that the open architecture may also permit the implementation of one or more additional modular utilities 13 in the operating control system 12 to enhance interaction between the therapy delivery system 10 and the individual using it. These modular utilities 13, for example, may allow determination of inputs/outputs accessible to the control algorithm in a form that assists with usability, entry efficiency, enhanced input detail, etc. For example, in one embodiment, a modular utility 13 may be an event module that stored data defining event-specific parameters for activities and/or foods or other events occurring in the individual's life style. In one embodiment, an event module stores data for various physiological conditions of the individual before, during, and/or after running for thirty minutes.

Figure 3:
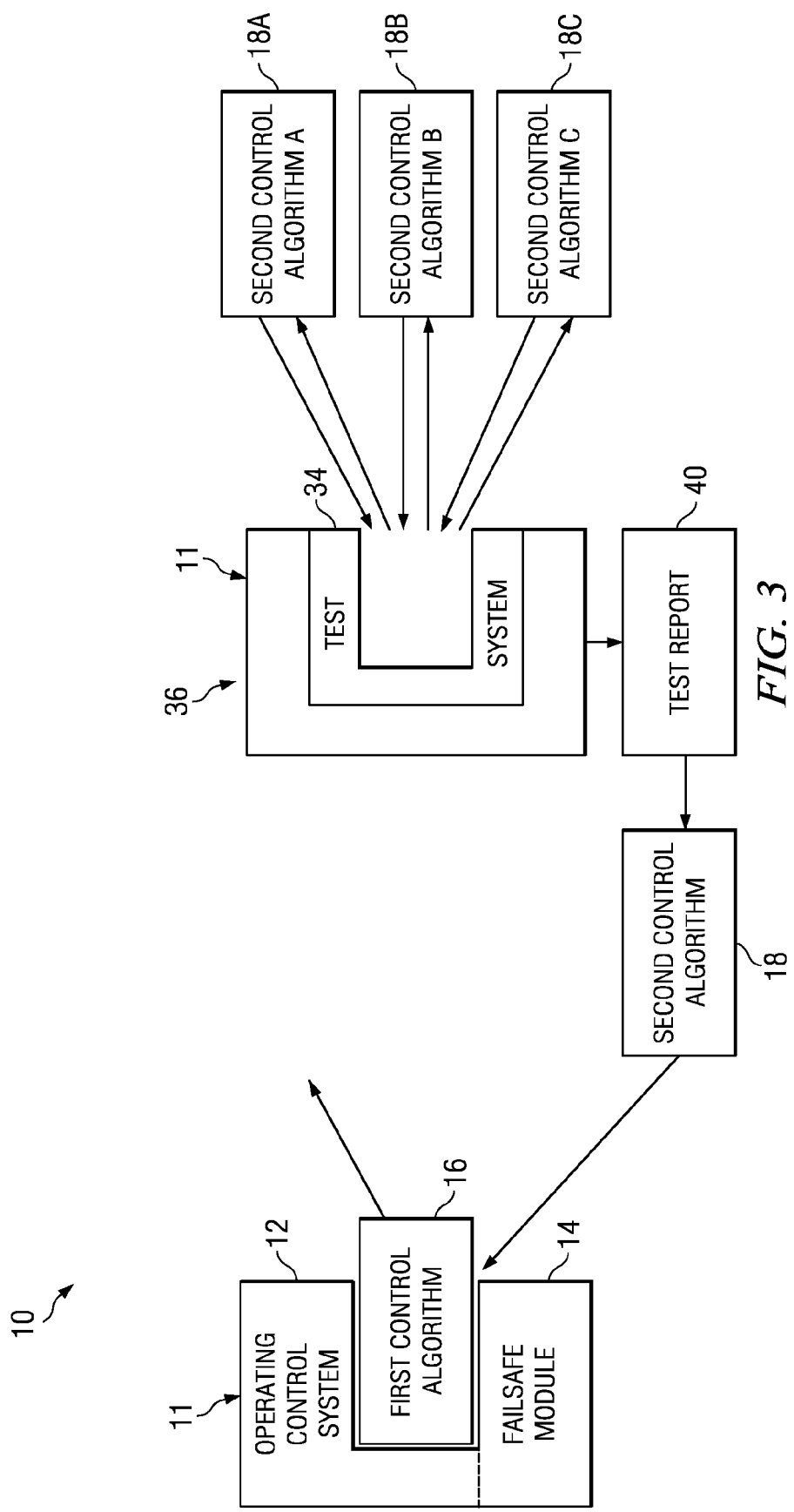
FIG. 3 is an illustration of a therapy delivery system according to another embodiment of the present invention.

Generally, the second control algorithm 18 that replaces the first control algorithm 16 is customized to the needs of the individual using the device. It is contemplated, however, that both the first control algorithm 16 and the second control algorithm 18 may be customized to the needs of the individual. Referring to FIG. 3, the second control algorithm 18 is customized through testing in a simulation module 36. This simulation module 36 provides a test environment simulating at least one or more physiological conditions of the individual and enables testing of the second control algorithm 18 when implemented in the therapy dosage module 11 in the test environment. Thereby, the second control algorithm 18 is tested before being used in the therapy delivery system 10 to deliver therapy to the individual. It is further contemplated that both the first control algorithm 16 and the second control algorithm 18 may be customized to the needs of the individual prior to determination of the therapy through testing in the test environment.

Figure 4:
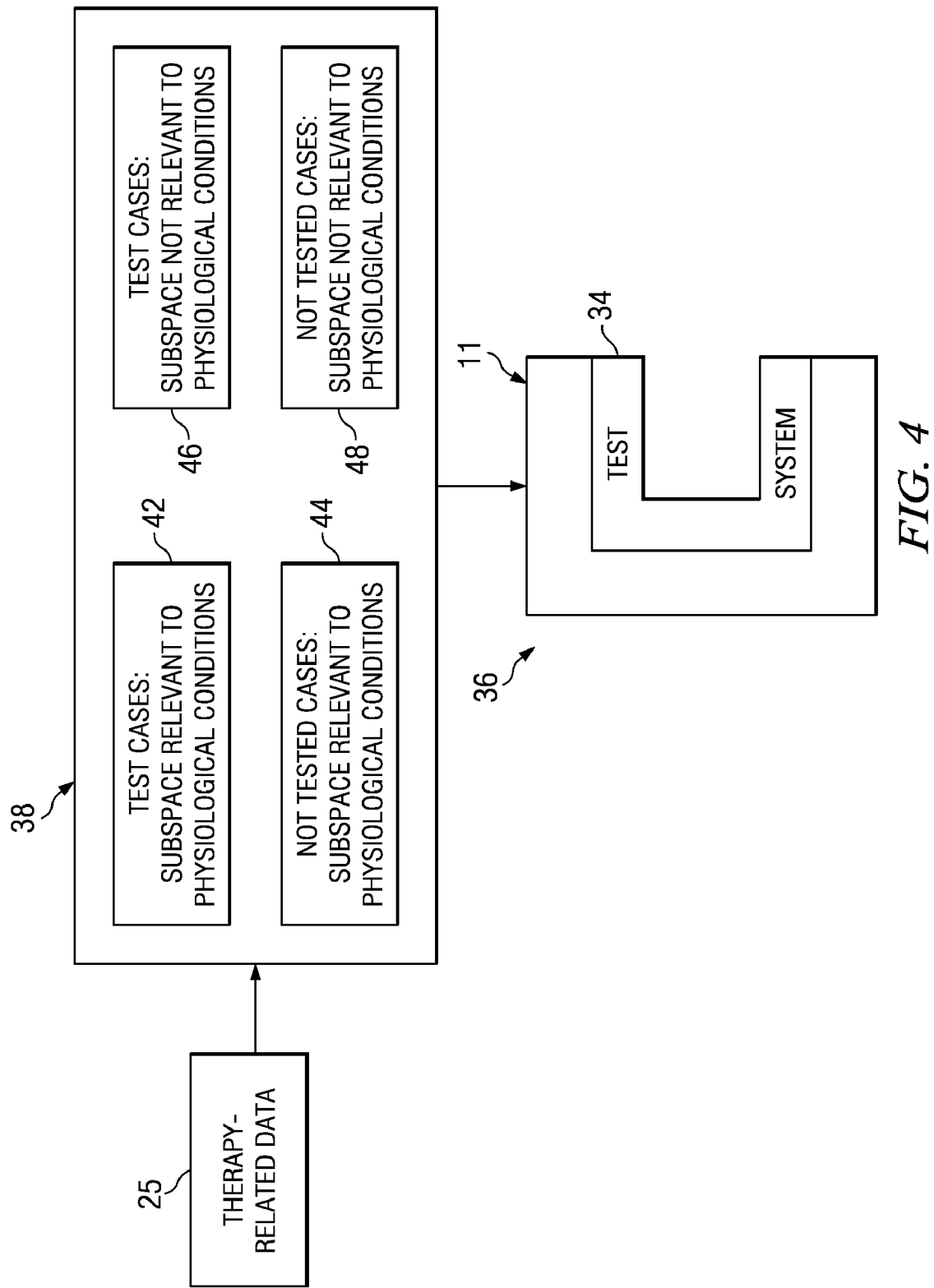
FIG. 4 is an illustration of a test system suite and a simulation module of a therapy delivery system according to one embodiment of the present invention.

The testing of the second control algorithm 18 in the simulation module 36 comprises implementing the second control algorithm 18 in one or more test systems 34 and applying the test systems 34 to a virtual patient population of the test environment. As shown in FIG. 4, the simulation module 36 may be validated to substantially account for all physiologically relevant test cases. Test cases, which generally comprise target population analysis data, are incorporated into test environments provided by the simulation module 36 such that the virtual patient population substantially accounts for all cases relevant to safe usage of the tested control algorithms and/or changes in parameters/parameter ranges. It is to be appreciated that test cases additionally cover those test cases used to examine logical changes to the algorithm, and/or use-cases not foreseen and/or specific to an algorithm on order to excite new logic.

FIG. 4 illustrates that, in addition to therapy-related data 25 specific to the individual, test cases covering a subspace relevant to physiological conditions 42, not tested cases covering subspace relevant to physiological conditions 44, test cases covering subspace not relevant to physiological conditions 46, and not tested cases covering subspace not relevant to physiological conditions 48 are incorporated into the test environments. The test cases 42, 44, 46, 48 should cover the operating space to test all physiologically relevant cases. Rules for encompassing the operational range to ensure correct therapy for all relevant cases within the operational space should also be provided. For example, as test cases 44 may impact the end user, care should be taken to avoid missing critical cases, wherein rule can check for such instances, whereas test cases 46, 48 do not impact the end user and thus checking may be unnecessary. The test cases 42, 46 and not tested cases 44, 48 may be updated as necessary with new target population analysis data and/or therapy-related regulation requirements. Further details concerning test cases development, updating, and usage suitable for the present invention is disclosed by commonly assigned and co-pending U.S. patent application Ser. No. 12/119,201, entitled "MEDICAL DIAGNOSIS, THERAPY, AND PROGNOSIS SYSTEM FOR INVOKED EVENTS AND METHODS THEREOF," which the entire disclosure thereof is herein fully incorporated by reference.

The testing of the second control algorithm 18 identifies any detrimental outcomes to patient health caused by the therapy determined by the second control algorithm 18 and any detrimental parameters of the second control algorithm 18 prior to usage in the therapy delivery system 10 to deliver therapy to the individual. The identified detrimental outcomes and/or parameters may be set forth in a test report 40 generated by the simulation module 36. The second control algorithm 18 may be modified as necessary to substantially eliminate the detrimental outcomes, if any, identified by the simulation module 36. If modified, the second control algorithm 18 may be undergo additional testing in the simulation module 36 to substantially ensure proper modification of the control algorithm 18. Thereafter, the second control algorithm 18 may be implemented with a therapy dosage module 11 in the therapy delivery system 10, replacing the first control algorithm 16. While only the second control algorithm 18 is shown in FIG. 3 as being tested in the simulation module 36, it is contemplated that the first control algorithm 16, or any other control algorithm that may be utilized by the therapy delivery system 10, may be tested before being used in the therapy delivery system 10 to deliver therapy to the individual and that the simulation module 36 may enable testing of both the first and second control algorithms 16, 18 when implemented in the test environment.

Figure 2:
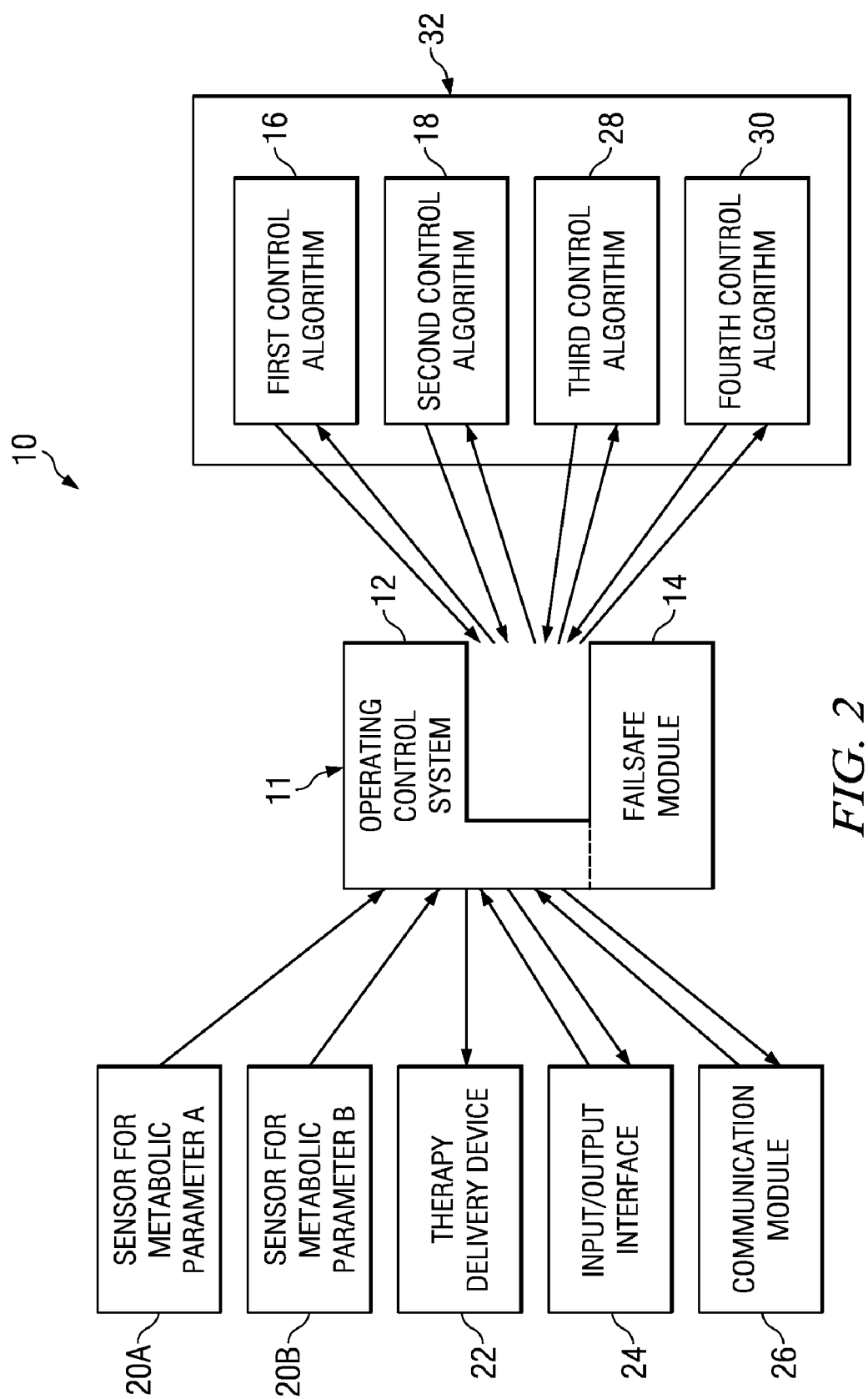
FIG. 2 is an illustration of a therapy delivery system according to another embodiment of the present invention.

According to one embodiment of the therapy delivery system 10, shown in FIG. 2, the first control algorithm 16, the second control algorithm 18, or both, is selectable by the individual from a predefined list 32 of control algorithms customized to the needs of the individual. This predefined list 32 may include any number of such control algorithms so that the individual or physician may replace a previously selected control algorithm with another so as to enhance therapy determination for the individual.

For example, FIG. 2 illustrates a predefined list 32 of individually selectable first, second, third, and fourth control algorithms 16, 18, 28, 30 uniquely defined to determine therapy for the individual when selected and implemented in the therapy dosage module 11 of the therapy delivery system 10. Further, the predefined list 32 of customized control algorithms can be uniquely defined from data such as, but not limited to, analyses of target populations with which the individual may be identified, modifications to the analyses of target populations, and/or changes in therapy-related regulation requirements. In addition, parameters of any or all of the control algorithms included in the predefined list 32 may be modified for further customization to the needs of the individual. For example, one or more parameters of the first control algorithm 16, one or more parameters of the second control algorithm 18, or both, are modifiable to further customize the first control algorithm 16, the second control algorithm 18, or both, to the needs of the individual. The parameters/parameter ranges of the control algorithms may be used to define and/or formulate metabolic parameters, or other physiological conditions, of the individual or other therapy-related data, such as for example, but not limited to, patient physiology, meal information, carbohydrate intake, physical activity, and therapy infusion history. Generally, all such data is accessible to the control algorithms 16, 18 in determining therapy for the individual.

Alternatively, according to another embodiment of the therapy delivery system 10, the first control algorithm 16, the second control algorithm 18, or both, is defined independently and customized to the needs of the individual. More particularly, the first control algorithm 16, the second control algorithm 18, or both, are defined by data specific to the individual, rather than from analyses of target populations or other more generalized information. Further, one or more parameters of the independently defined first control algorithm, one or more parameters of the independently defined second control algorithm, or both, are modifiable to further customize the independently defined first control algorithm, the independently defined second control algorithm, or both, to the needs of the individual.

By way of example only, independently defined control algorithms may be defined by a physician who expresses to a manufacturer of such algorithms and/or therapy delivery systems an interest in using an independently defined control algorithm. The manufacturer can assist the physician in translating the intentions of the physicians into a control algorithm having a form conducive for implementation in an open architecture of an operating control system of a therapy dosage module while acknowledging the constraints of a therapy delivery system. The translation process and the resultant control algorithm may be unambiguously documented by the manufacturer to permit accurate and adequate evaluation of the control algorithm prior to usage in delivering therapy to an individual. Once defined, the control algorithm may be tested in a simulation module, or other algorithm testing module, as described above to ensure compatibility with a therapy dosage module of a therapy delivery system and to identify possible detrimental patient outcomes and/or algorithm parameters. If desired, the simulation module may be verified under a standard validation protocol, as described above with reference to FIG. 4. Once any necessary modifications to the control algorithm are completed and usage of the control algorithm is approved by the manufacturer and/or the physician following additional testing, the manufacturer may require the physician to sign documentation, such as, but not necessarily limited to, a release permitting the manufacturer to share all information related to the translation, formulation, testing, and approval processes with relevant regulatory agencies and a statement that the control algorithm and/or the therapy delivery system utilizing such algorithm are to be used only for clinical research under the responsibility of the physician. Thereafter, the manufacturer may implement the control algorithm in the physician's therapy delivery system and inform the relevant regulatory agencies of the above-described processes and implementation.

In another embodiment, the present invention is suitable for use with test protocols that cover/identify the safe operation of an algorithm as a go/no go criteria. In such an embodiment, it is envisioned that algorithms which satisfy the test protocol should be acceptable for direct deployment in field.

As mentioned above, the therapy dosage module 11 of the therapy delivery system 10 comprises an operating control system 12 and a failsafe module 14. The failsafe module 14 defines one or more therapy limitations independent of the first and second control algorithms 16, 18 for substantially preventing delivery of the therapy outside of the therapy limitations. These therapy limitations may be specific to the individual and define the limitations of permissible therapy that may be delivered while avoiding substantial harm to the individual. Thereby, the failsafe module 14 safeguards against the delivery of therapy in amounts, concentrations, rates, etc. that may result in detrimental outcomes in the health of the individual. Should the failsafe module 14 prevent the delivery of a therapy determined by the first or second control algorithm 16, 18, the failsafe module 14 may transmit a signal through the operating control system 12 to the input/output interface 24 to notify the individual of the prevention of the therapy delivery and of the possible need for the individual to contact a physician and/or direct the delivery of another therapy, whether predefined or independently defined.

The input/output interface 24 of the therapy delivery system 10 is provided for exchanging therapy-related data with the individual, such as the notification of a prevention of a therapy delivery or the direction to delivery a therapy, as mentioned above. More particularly, the input/output interface 24 receives data relating to physiological conditions, meals, and/or activities of the individual. Such data, for example, may be sensed by the metabolic sensor 20A, directly inputted by the individual, or transmitted by the communication module 26 from another electronic or digital source. In addition, the input/output interface 24 displays data relating to physiological conditions of the individual, meals, recommended and/or delivered therapies, and/or a list of control algorithms approved for implementation in the therapy dosage module 11 of the therapy delivery system 10. As such, the input/output interface 24 generally is in communication, either wired or wireless, to the failsafe module 14, the metabolic sensor 20A, the therapy delivery device, 22, and the communication module 26 through the operating control system 12 of the therapy dosage module 11.

The metabolic sensor 20A of the therapy delivery system 10 is provided for sensing a metabolic parameter of the individual. A metabolic parameter may be, but is not limited to, blood glucose level, blood pressure, or heart rate. In one embodiment, the metabolic sensor 20A senses blood glucose levels, or other metabolic parameter, of the individual on an intermittent basis. Alternatively, in another embodiment, the metabolic sensor 20A senses blood glucose levels, or other metabolic parameter, of the individual on a continual basis. In even yet another embodiment, the metabolic sensor 20A senses blood glucose levels, or other metabolic parameter, of the individual when directed by the individual or a physician through the input/output interface 24. Further, the therapy delivery system 10 may comprise one or more metabolic sensors to sense one or more metabolic parameters. For example, as shown in FIG. 2, the therapy delivery system may comprise two metabolic sensors 20A, 20B for sensing metabolic A and metabolic parameter B with both sensors 20A, 20B in communication with the operating control system 12 of the therapy dosage module 11. More particularly, the metabolic sensors 20A, 20B sense metabolic parameters A and B and transmit signals indicative of the condition of those parameters to the operating control system 12. The operating control system 12 may store these signals for a determined length of time for evaluation by the individual or a physician and/or for accessing by the control algorithms 16, 18 in determining therapy.

The communication module 26 of the therapy delivery system 10 may be provided for exchanging therapy-related data with a computer, portable device, network, or other related technology. For example, the communication module 26 may permit infrared transmission of data from the therapy delivery system 10 to a physician's computer so that the physician may have access to and evaluate data pertaining to sensed metabolic parameters, physiological conditions, and/or therapy delivery history. Likewise, the communication module 26 may permit the individual or physician to transmit meal-specific data, such as carbohydrate content, from a computer to the therapy delivery system 10 for storage and ready access by the individual when inputting through the input/output interface 24 a proposed meal to enhance therapy determination by the system 10.

The therapy delivery device 22 of the therapy delivery system 10 is provided for delivering the therapy determined by the first or second control algorithm 16, 18 of the therapy dosage module 11. Generally, as shown in FIGS. 1 and 2, the therapy delivery device 22 receives direction from the operating control system 12 to provide therapy in an amount, in a concentration, at a delivery rate, and/or on a delivery schedule, as determined by the first or second control algorithm 16, 18.

The delivery of therapy by the therapy delivery device 22 may also be affected by the operational functionality of the therapy delivery system 10. More particularly, the therapy delivery system 10 may operate in a semi-closed loop fashion or a fully closed loop fashion. Although the therapy delivery device 22 generally is able to provide continuous therapy delivery, such as continuous subcutaneous insulin infusion (CSII mode), the delivery device 22 can be used to emulate an intensive therapy regimen of several therapies per day (MDI emulation mode). As such, an individual utilizing a therapy delivery system 10 operating in the MDI emulation mode, or in a semi-closed loop fashion, generally must approve every therapy recommended by the control algorithm 16, 18 of the system 10 before the therapy is delivered to the individual by the therapy delivery device 22. Use of a therapy delivery system 10 operating in the MDI emulation mode may ease an individual's and/or physician's transition from use of an established multiple therapy delivery regimen to an embodiment of the therapy delivery system 10.

An individual utilizing a therapy delivery system 10 operating in the CSII mode, or in a fully closed loop fashion, however, generally receives therapy delivery on an automated basis without prior approval from the individual. This generally is due to the therapy delivery system 10 operating in the CSII mode frequently adjusting therapies for the individual on a continuous, or substantially continuous, basis as the individual's sensed metabolic parameters and/or other physiological conditions change. Since such adjustments in therapies may occur on a relatively high frequency, it is unlikely that the individual could approve every recommended therapy delivery. However, it is to be appreciated that high frequency is not the only reason. Adjustments in therapy may be also sporadic or sparse and in that case automation is useful especially in cases where the delivery amount, which meet certain failsafe guidelines, do not need user approval such as, for example, basal delivery cases. Therefore, the therapy delivery in one embodiment occurs on an automated basis with such deliveries generally subject to the failsafe module 14 and the defined therapy limitations described above.

The therapy delivery system 10 may also operate in a monitor only/no feedback mode. In this mode, the system's 10 sensing and monitoring capabilities, along with inputted data, may be completely ignored. Here, the therapy delivery system 10 is used as a continuous metabolic parameter sensor and a separate stand-alone therapy delivery device 22. The therapy delivery device 22 is controlled through an input/output interface 24 and trends in the metabolic parameter are sensed and displayed through the input/output interface 24 of the system 10. In addition, signals for notifying the individual of potential or oncoming detrimental health outcomes, such as alarms for oncoming hypoglycemic or hyperglycemic conditions, are enabled. Also, sensed metabolic parameters and delivered therapies are stored by the operating control system 12 of the therapy delivery system 10. This monitor only/no feedback mode of operation may be used for purposes such as, but not limited to: optimizing an individual's therapy regimen; establishing therapy delivery programs for the therapy delivery device 22; using the therapy delivery system 10 to monitor the individual for a specified length of time to determine an appropriate initial metabolic parameter setting before implementing one of the above-described operation modes of the therapy delivery system 10 (i.e., MDI emulation mode and CSII mode); and providing an individual and/or a physician with an opportunity to familiarize themselves with the therapy delivery system 10.

The therapy delivery system 10 may also permit various levels of interaction between the system 10 and an individual using it. For example, when the system 10 is utilized to continuously sense blood glucose concentration, data inputted by the individual regarding pending food intake or exercise would be helpful for the a control algorithm 16, 18 to maintain substantially stabilize blood glucose concentration. However, the willingness and/or ability of the individual to reliably input this data may vary from person-to-person. For example, a diabetic child is less likely to be willing and/or able to reliably input such data than a motivated, highly compliant adult. Therefore, it should be understood that there generally exists a trade-off between the achievable level of control over a metabolic parameter, such as blood glucose concentration, and the amount of interaction between the therapy delivery system 10 and the individual using it.

To further elaborate, two extreme cases are described. A first extreme case involves the use of a therapy delivery system 10 with no additional interaction between the system 10 and the individual. All insulin dosage adjustment decisions are based on the monitored blood glucose concentration and the previously delivered amounts of insulin and any general knowledge that the system 10 has acquired about the individual's life style. Without the additional interaction between the system 10 and the individual using it, meals cannot be anticipated and counteracted before an increase in the glucose concentration occurs and is monitored. As such, control over blood glucose concentration will be limited and somewhat sluggish.

A second extreme case involves the use of a therapy delivery system 10 with extensive interaction between the system 10 and the individual. With extensive interaction, before each meal, the individual inputs an estimate of the amount of carbohydrate intake associated with the proposed meal along with a statement about the type of food that is to be consumed with the meal. For example, a statement that the food is "light" may be understood by the system 10 that the food is easily digestible, like fruit, while a statement of "heavy" may be understood by the system 10 that the food is mixed with significant amounts of protein and/or fat. In addition, exercise is planned and inputted into the therapy delivery system 10 well in advance. Also, the system 10 may output a request to the individual at some time before the planned exercise that the individual confirm that the exercise is still expected to occur. The individual also inputs elevated stress levels, sickness, or other physiological conditions that may affect prospective insulin infusion. The input/output interface of the therapy delivery system 10 and the operating control system 12 are designed to keep the interaction as intuitive, simple, and fast as possible. Since the system 10 knows about meals beforehand, it can react much more effectively to prevent post prandial hyperglycemic excursions. In addition, before a scheduled exercise period, the system 10 can appropriately reduce the insulin infusion to avoid strong glucose excursions into the hypoglycemic region. The achievable overall level of control will be superior to that of the system with less interaction with the individual.

Figure 5:
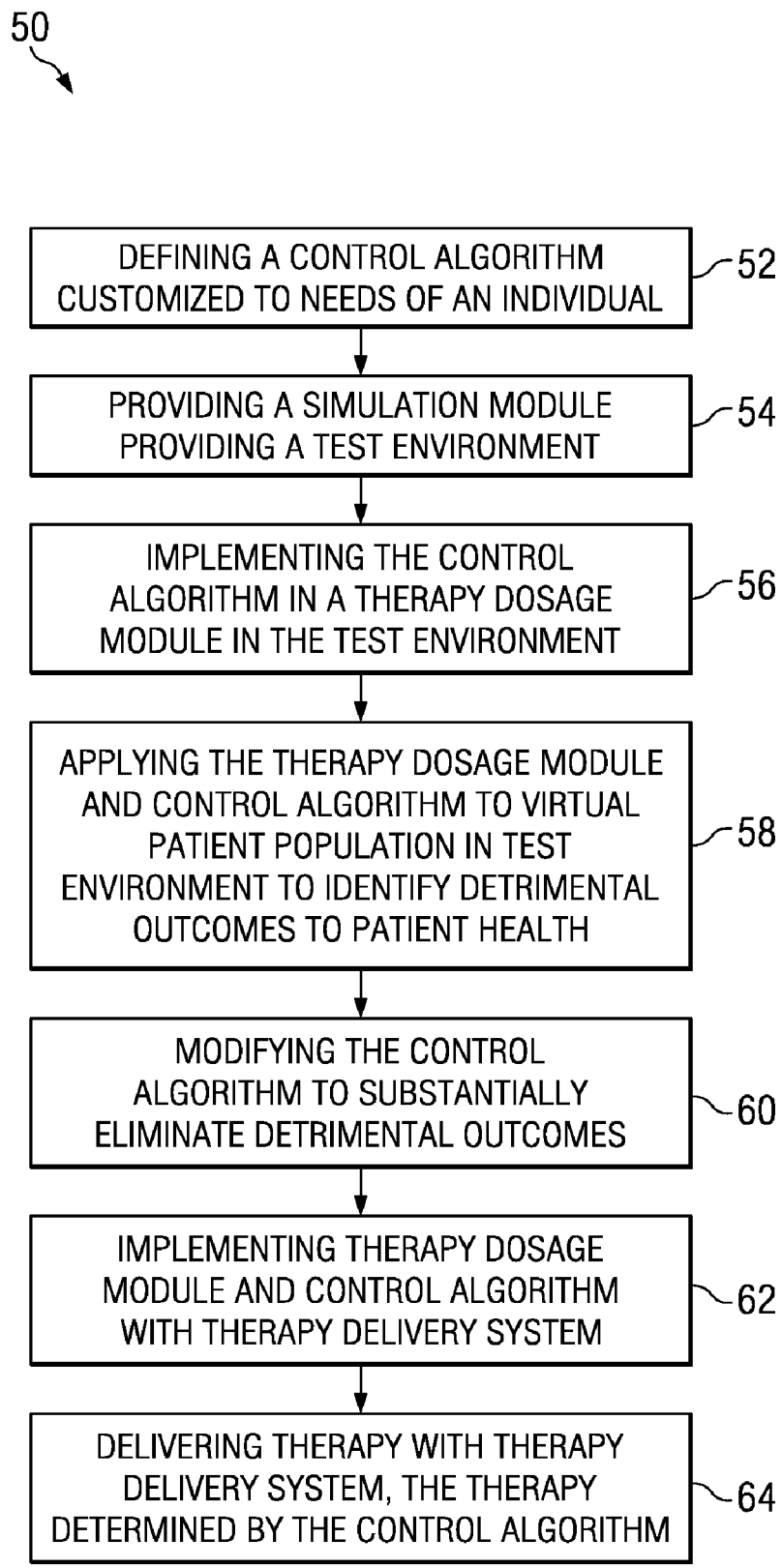
FIG. 5 is a process chart of a method delivering therapy to an individual with a therapy delivery system according to one embodiment of the present invention.

In accordance with another embodiment, shown in FIG. 5, a method 50 of delivering therapy to an individual with an embodiment of a therapy delivery system is provided. The method generally comprises a control algorithm being defined for determining therapy for the individual, wherein the control algorithm is customized to the needs of the individual in step 52. A simulation module in step 54 is provided for providing a test environment simulating at least one or more physiological conditions of the individual according to a simulation protocol. The simulation protocol in one embodiment can cover a patient day to day activity such as meals with amount, composition, insulin therapy, medication, exercise. In other embodiments, the simulation protocol may just cover certain combinations critical in understanding therapy decision. In addition, the simulation protocol can be limited to short duration such as few hours to long simulations covering few days to many days to many months depending on use-case. The control algorithm may then be implemented in a therapy dosage module in the test environment in step 56. The therapy dosage module and the control algorithm generally are then applied to a virtual patient population in the test environment to identify any detrimental outcomes to patient health caused by the therapy determined by the control algorithm prior to usage of the control algorithm in the therapy delivery system to deliver the therapy to the individual in step 58. The control algorithm may be modified as necessary to substantially eliminate the detrimental outcomes, if any, identified by the simulation module in step 60. The therapy dosage module and the control algorithm are then implemented with the therapy delivery system in step 62. This permits the delivering therapy to the individual with the therapy delivery system, the therapy determined by the control algorithm in step 64.

The method 50 may further comprise comparing the therapy determined by the control algorithm with one or more therapy limitations independently defined by a failsafe module prior to delivery of the determined therapy to substantially prevent delivery of therapy outside of the defined therapy limitations. The method 50 may also comprise replacing the control algorithm in the therapy dosage module with a second control algorithm further customized to the needs of the individual.

While repeated reference is made herein to a first control algorithm and a second control algorithm, it is contemplated that any number of control algorithms may be defined, tested, implemented, and/or used with embodiments of the therapy delivery system of the present invention. In addition, any one control algorithm may be replaced with any other control algorithm in accordance with the present invention.

It is noted that recitations herein of a component of the present invention being "configured" in a particular way or to embody a particular property, or function in a particular manner, are structural recitations as opposed to recitations of intended use. More specifically, the references herein to the manner in which a component is "configured" denotes an existing physical condition of the component and, as such, is to be taken as a definite recitation of the structural characteristics of the component.

It is noted that terms like "generally" and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present invention or to emphasize alternative or additional features that may or may not be utilized in a particular embodiment of the present invention.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

The foregoing description of the invention has been presented for purposes of illustration and description. It is not intended to be exhaustive or to limit the invention to the precise form disclosed, and other modifications and variations may be possible in light of the above teachings. The above embodiments disclosed were chosen and described to explain the principles of the invention and its practical application to thereby enable others skilled in the art to best utilize the invention. It is intended that the appended claims be construed to include other alternative embodiments of the invention except insofar as limited by the prior art. Therefore, having described the invention in detail and by reference to specific embodiments thereof, it will be apparent that modifications and variations are possible without departing from the scope of the invention defined in the appended claims.

What is claimed is:

1. A therapy delivery system for an individual comprising:
a therapy dosage module comprising an operating control system having an open architecture which supports operation of the therapy delivery system and which has a first control algorithm replaceable with a second control algorithm customized to needs of the individual, the first and second control algorithms being defined to determine therapy for the individual, wherein the open architecture of the operating control system provides a logical separation of the first and second control algorithm such that the first control algorithm is removable from the operating control system and replaceable by the second control algorithm without interfering with an operational functionality of hardware or software of the therapy delivery system; and
a simulation module providing a test environment which simulates at least one or more physiological conditions of the individual and enables testing of the second control algorithm when implemented in the therapy dosage module in the test environment before being used in the therapy delivery system to deliver the therapy determined by the second control algorithm to the individual, wherein:
the testing of the second control algorithm in the simulation module comprises using the second control algorithm on a virtual patient population of the test environment, and identifying any detrimental outcomes to patient health in the virtual patient population caused by the therapy determined by the second control algorithm prior to usage in the therapy delivery system to deliver therapy to the individual;
wherein the therapy dosage module comprises a failsafe module defining one or more therapy limitations independent of the first and second control algorithms which prevents delivery of therapy outside of the therapy limitations.

2. The therapy delivery system according to claim 1, wherein the first control algorithm, the second control algorithm, or both, is selectable by the individual from a predefined list of control algorithms customized to the needs of the individual.

3. The therapy delivery system according to claim 2, wherein one or more parameters of the first control algorithm, one or more parameters of the second control algorithm, or both, are modifiable to further customize the first control algorithm, the second control algorithm, or both, to the needs of the individual.

4. The therapy delivery system according to claim 1, wherein the first control algorithm, the second control algorithm, or both, is defined independently and customized to the needs of the individual.

5. The therapy delivery system according to claim 4, wherein one or more parameters of the independently defined first control algorithm, one or more parameters of the independently defined second control algorithm, or both, are modifiable to further customize the independently defined first control algorithm, the independently defined second control algorithm, or both, to the needs of the individual.

6. The therapy delivery system according to claim 1, wherein the simulation module enables testing of both the first and second control algorithms when implemented in the therapy dosage module in the test environment.

7. The therapy delivery system according to claim 1, wherein therapy delivered to the individual by the therapy delivery system is a dosage amount, concentration, delivery rate, specific time, and/or delivery schedule of a drug determined by the first or second control algorithm.

8. The therapy delivery system according to claim 1, wherein both the first control algorithm and the second control algorithm are customized to the needs of the individual.

9. The therapy delivery system according to claim 1, wherein the therapy delivery system requires the individual to approve therapy determined by the first or second control algorithm prior to delivery of the determined therapy.

10. The therapy delivery system according to claim 1, wherein the therapy delivery system further comprises an input/output interface for exchanging therapy-related data with the individual.

11. The therapy delivery system according to claim 10, wherein the input/output interface receives data relating to physiological conditions, meals, and/or activities of the individual, this received data being accessible to the first or second control algorithm in determining the therapy.

12. The therapy delivery system according to claim 10, wherein the input/output interface displays data relating to physiological conditions of the individual, meals, recommended and/or delivered therapies, and/or a list of control algorithms approved for implementation in the therapy dosage module of the therapy delivery system.

13. The therapy delivery system according to claim 1, wherein the therapy delivery system further comprises a communication module for exchanging therapy-related data with a computer, portable device, network, or other related technology.

14. The therapy delivery system according to claim 1, wherein the therapy delivery system further comprises one or more metabolic sensors for sensing one or more metabolic parameters of the individual.

15. The therapy delivery system according to claim 1, wherein the therapy delivery system further comprises one or more therapy delivery devices for delivering therapy determined by the first or second control algorithm of the therapy dosage module.

16. The therapy delivery system of claim 1 wherein the therapy dosage module further comprises a modular utility to enhance interaction between the therapy delivery system and the individual.

17. The therapy delivery system of claim 16, wherein the modular utility provides accessibility to control algorithms.

18. The therapy delivery system of claim 16, wherein the modular utility is an event module.

19. The therapy delivery system of claim 18, wherein the event module stores data for physiological conditions of the individual.

20. The therapy delivery system of claim 1 wherein the therapy delivery system delivers therapy determined by the first or second control algorithm without requiring approval from the individual prior to delivery of the determined therapy.

21. A therapy delivery system for an individual comprising:
a metabolic sensor which senses a metabolic parameter of the individual on an intermittent or continual basis;
an input/output interface which exchanges therapy-related data with the individual;
a therapy dosage module comprising an operating control system having an open architecture which supports operation of the therapy delivery system and which has a first control algorithm replaceable with a second control algorithm, the first and second control algorithms being defined to determine therapy for the individual, wherein the open architecture of the operating control system provides a logical separation of the first and second control algorithm such that the first control algorithm is removable from the operating control system and replaceable by the second control algorithm without interfering with an operational functionality of hardware or software of the therapy delivery system;
a therapy delivery device which delivers the therapy determined by the first or second control algorithm of the therapy dosage module,
wherein the second control algorithm is customized to needs of the individual prior to determination of the therapy through testing of the second control algorithm in a test environment simulating at least one or more physiological conditions of the individual, and wherein both the first control algorithm and the second control algorithm are customized to the needs of the individual prior to determination of the therapy through testing in the test environment, and
wherein the therapy dosage module comprises a failsafe module defining one or more therapy limitations independent of the first and second control algorithms which prevents delivery of therapy outside of the therapy limitations.

22. The therapy delivery system of claim 21 wherein the therapy dosage module further comprises a modular utility to enhance interaction between the therapy delivery system and the individual.

* * * * *

UNITED STATES PATENT AND TRADEMARK OFFICE
CERTIFICATE OF CORRECTION

PATENT NO. : 8,123,717 B2
APPLICATION NO. : 12/121199
DATED : February 28, 2012
INVENTOR(S) : Stefan Weinert et al.

Page 1 of 1

It is certified that error appears in the above-identified patent and that said Letters Patent is hereby corrected as shown below:

Col. 1, Line 44, "evaluated and approve" should read --evaluated and approved--;

Col. 5, Line 50, "may be undergo" should read --may undergo--;

Col. 7, Line 42, "direction to delivery a therapy" should read --direction to deliver a therapy--;

Col. 7, Line 56, "device, 22" should read --device 22--;

Col. 9, Line 47, "helpful for the a control" should read --helpful for the control--;

Col. 9, Line 48, "substantially stabilize" should read --substantially stabilized--;

Col. 9, Line 50, "person-to-person" should read --person to person--;

Col. 10, Line 42, "patient day to day activity" should read --patient day-to-day activity--; and Col. 10, Line 61, "permits the delivering therapy" should read --permits the delivery therapy--.

Signed and Sealed this
Tenth Day of July, 2012

David J. Kappos
*Director of the United States Patent and Trademark Office*